United States Patent [19]

Alaimo et al.

[11] 4,339,386
[45] Jul. 13, 1982

[54] 5-[(3,4-DIMETHOXYPHENYL)OR(4-CHLOROPHENYL)]-2-FURANCARBOXALDEHYDE-O-[(METHYLAMINO)CARBONYL]OXIME

[75] Inventors: Robert J. Alaimo; Joseph E. Gray, both of Norwich, N.Y.

[73] Assignee: Morton-Norwich Products, Inc., Norwich, N.Y.

[21] Appl. No.: 290,409

[22] Filed: Aug. 5, 1981

[51] Int. Cl.³ .......................................... C07D 307/54
[52] U.S. Cl. .................................. 549/496; 424/285; 549/491
[58] Field of Search ...................... 260/347.3, 347.7

[56] References Cited

U.S. PATENT DOCUMENTS 3,906,010  9/1975  Pelosi et al. ............... 260/347.5
4,012,415  3/1977  Pelosi et al. ............... 260/347.7 X Primary Examiner—Richard Raymond
Attorney, Agent, or Firm—Anthony J. Franze

[57] ABSTRACT

Compounds of the formula:

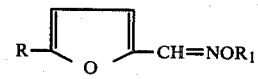

wherein R is 4-chlorophenyl, 3,4-dichlorophenyl, or 3,4-dimethoxyphenyl, and $R_1$ is hydrogen or methylaminocarbonyl with the proviso that when R is 4-chlorophenyl, $R_1$ is methylaminocarbonyl are useful as antifungal agents.

2 Claims, No Drawings

5-[(3,4-DIMETHOXYPHENYL)OR(4-CHLOROPHENYL)]-2-FURANCARBOXALDEHYDE-O-[(METHYLAMINO)CARBONYL]OXIME

This invention is concerned with chemical compounds and particularly with compounds of the formula:

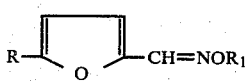

wherein R is 4-chlorophenyl, 3,4-dichlorophenyl, or 3,4-dimethoxyphenyl, and $R_1$ is hydrogen or methylaminocarbonyl with the proviso that when R is 4-chlorophenyl, $R_1$ is methylaminocarbonyl.

These compounds possess antifungal activity. For example in the commonly employed in vitro technique for assaying antifungal potency a concentration of from 10–100 mcg per milliliter of media inhibits the growth of *Microsporum canis*. They are thus adapted to be combined in various forms such as elixirs, dusts, suspensions, ointments and the like for application to locales where the control of fungus is desirable.

The methods now preferred for the preparation of the compounds of this invention are set forth in the following examples.

EXAMPLE I

5-(3,4-Dimethoxyphenyl)-2-furancarboxaldehyde-O-[(methylamino)carbonyl]oxime A. 5-(3,4-Dimethoxyphenyl)-2-furaldehyde A 12 l. four-necked flask equipped with a stirrer, a thermometer and a dropping funnel was charged with water (5 l.). Hydrochloric acid (500 ml) was introduced dropwise. 3,4-dimethoxyaniline hydrochloride (379 g, 2.0 moles) was introduced. This mixture was cooled to −5° C. with a mixture of dry ice and acetone. A solution of sodium nitrite (200 g, 2.9 moles) in water (1600 ml) was introduced dropwise maintaining the temperature at −5° to 0° C. This was followed by the addition of furaldehyde (384 g, 4.0 moles) at −5° C. as fast as possible. A solution of $CuCl_2.2H_2O$ (112 g) in water (500 ml) was introduced. Stirring was continued for 8 days at ambient temperature. The contents of the flask was extracted with ether (3×3 l.). The combined extracts were dried over $MgSO_4$ overnight. The mixture was filtered and the drying agent was washed with anhydrous ether. The solvent was removed in vacuo. The excess furfural was removed by using an oil pump and a water bath having a maximum temperature of 63° C. The residue was triturated with a minimum amount of isopropanol and ice cooled. The semi-solid was filtered off and washed with isopropanol. The obtained solid was stirred with fresh isopropanol (500 ml) and filtered to give 125 g of the product (27%).

B. 5-(3,4-Dimethoxyphenyl)furylformaldoxime 5-(3,4-Dimethoxyphenyl)furaldehyde (100 g, 0.43 mole), hydroxylamine hydrochloride (59.9 g, 0.86 mole) and anhydrous sodium acetate (70.69 g) was treated with solution of water (150 ml) in SDA #32 (2200 ml). The reaction mixture was heated at reflux for 6 hours. The mixture was filtered hot and the filtrate chilled. The intermediate was collected and used without further purification in Part B; 38 g (36%), m.p. 148°.

C. 5-(3,4-Dimethoxyphenyl)-2-furancarboxaldehyde-O-[(methylamino)-carbonyl]oxime 5-(3,4-Dimethoxyphenyl)furylformaldoxime (9.5 g, 0.038 mole) and DMF (500 ml) was treated with methyl isocyanate (16 ml, 0.27 mole). The solution was stirred at room temperature for 4 hours and at steam bath temperature for 1 hour. The reaction solution was poured into 3 liters of water. The tan precipitate was collected to give 6 g (51%) of product.

An analytical sample was prepared by one recrystallization from SDA #32, m.p. 163°–164°.

Anal. Calc'd for $C_{15}H_{16}N_2O_5$: C, 59.21; H, 5.30; N, 9.21. Found: C, 60.08; H, 5.39; N, 8.80.

EXAMPLE II

5-(4-Chlorophenyl)-2-furancarboxaldehyde-O-[(methylamino)carbonyl]oxime 5-(3,4-Dichlorophenyl)furylaldehyde (15 g, 0.06 mole), hydroxylamine hydrochloride (8.66 g, 0.12 mole) and anhydrous sodium acetate (10.2 g, 0.12 mole) was treated with SDA #32 (318 ml) and water (22 ml). The reaction mixture was heated at reflux for 3 hours. The mixture was filtered hot. The filtrate formed a precipitate after treatment with water. The product was filtered, yield 12.9 g (84%).

An analytical sample was prepared by one recrystallization from isopropyl alcohol, m.p. 149°–153°.

Anal. Calc'd. for $C_{11}H_7Cl_2NO_2$: C, 51.59; H, 2.76; N, 5.47. Found: C, 51.64; H, 2.67; N, 5.39.

EXAMPLE III

5-(4-Chlorophenyl)-2-furancarboxaldehyde-O-[(methylamino)carbonyl]oxime (4-Chlorophenyl)furylformaldoxime and 1 liter of anhydrous ether was maintained at 5°. The reaction was treated with methyl isocyanate. The reaction was stirred for 15 minutes at 5°, then 3 hours at 35°. The product was filtered; 12 g (68%).

An analytical sample was prepared by two recrystallizations from toluene, m.p. 115°.

Anal. Calc'd. for $C_{13}H_{11}ClN_2O_3$: C, 56.03; H, 3.98; N, 10.05. Found: C, 55.88; H, 4.01; N, 10.08.

What is claimed is:

1. The compound 5-(3,4-dimethoxyphenyl)-2-furancarboxaldehyde-O-[(methylamino)carbonyl]oxime.

2. The compound 5-(4-chlorophenyl)-2-furancarboxaldehyde-O-[(methylamino)carbonyl]oxime.

* * * * *